United States Patent
Park et al.

(10) Patent No.: US 10,392,648 B2
(45) Date of Patent: Aug. 27, 2019

(54) AIRBORNE MICROBIAL MEASUREMENT APPARATUS AND MEASUREMENT METHOD

(71) Applicants: LG ELECTRONICS INC., Seoul (KR); INDUSTRY-ACADEMIC COOPERATION FOUNDATION, YONSEI UNIVERSITY, Seoul (KR)

(72) Inventors: Chulwoo Park, Seoul (KR); Yeekyeong Jung, Seoul (KR); Sunghwa Lee, Seoul (KR); Jungho Hwang, Seoul (KR); Jiwoon Park, Seoul (KR)

(73) Assignees: LG ELECTRONICS INC., Seoul (KR); INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 252 days.

(21) Appl. No.: 15/120,073

(22) PCT Filed: Dec. 16, 2014

(86) PCT No.: PCT/KR2014/012421
§ 371 (c)(1),
(2) Date: Aug. 18, 2016

(87) PCT Pub. No.: WO2015/130002
PCT Pub. Date: Sep. 3, 2015

(65) Prior Publication Data
US 2017/0058315 A1   Mar. 2, 2017

(30) Foreign Application Priority Data
Feb. 27, 2014 (KR) .................. 10-2014-0023203

(51) Int. Cl.
*C12Q 1/24* (2006.01)
*G01N 1/22* (2006.01)

(52) U.S. Cl.
CPC .............. *C12Q 1/24* (2013.01); *G01N 1/22* (2013.01)

(58) Field of Classification Search
CPC .................................. C12Q 1/24; G01N 1/22
See application file for complete search history.

(56) References Cited

U.S. PATENT DOCUMENTS

| 5,773,710 A | 6/1998 | Squirrell |
| 5,918,259 A | 6/1999 | Squirrell |

(Continued)

FOREIGN PATENT DOCUMENTS

| EP | 2 343 381 A1 | 7/2011 |
| JP | 2011-155970 A | 8/2011 |

(Continued)

*Primary Examiner* — Michael L Hobbs
(74) *Attorney, Agent, or Firm* — Dentons US LLP (57) ABSTRACT

Provided are an airborne microbial measurement apparatus and a method of measuring the same. The airborne microbial measurement apparatus includes a particle separation device including a main body having a flow space in which airborne microorganism flows and a collection unit separably coupled to one side of the main body to collect the airborne microorganism, a reagent container in which a lysis reagent reacting with the airborne microorganism collected in the collection unit and a luminous material are stored, and a luminescence measurement device for measuring intensity of light emitted after the airborne microorganism reacts with the lysis reagent and the luminous material.

10 Claims, 4 Drawing Sheets

(56) References Cited

U.S. PATENT DOCUMENTS

| | | | |
|---|---|---|---|
| 2005/0136507 A1 | 6/2005 | Sullivan et al. | |
| 2013/0316393 A1* | 11/2013 | Swanson | C12Q 1/04 435/34 |
| 2014/0017723 A1 | 1/2014 | Hwang et al. | |
| 2014/0206034 A1* | 7/2014 | Gordon | C12Q 1/24 435/30 |

FOREIGN PATENT DOCUMENTS

| | | |
|---|---|---|
| JP | 2012-44971 A | 3/2012 |
| JP | 2013-130435 A | 7/2013 |
| KR | 10-2006-0022302 A | 3/2006 |
| KR | 10-2012-0086384 A | 8/2012 |
| KR | 10-2012-0128619 A | 11/2012 |
| WO | 2012/102448 A1 | 8/2012 |
| WO | 2013/132630 A1 | 9/2013 |
| WO | 2013/065497 A1 | 4/2015 |
| WO | 2015/130000 A1 | 9/2015 |

\* cited by examiner

[Fig. 1]

PRIOR ART

```
START
  ↓
APPLY VOLTAGE INTO ELECTRIC CHARGE PART —— S11
  ↓
OPERATE FLOW GENERATION UNIT —— S12
  ↓
MOVE ELECTRICALLY CHARGED AIRBORNE
MICROORGANISM INTO INSERTION HOLE —— S13
  ↓
COLLECT AIRBORNE MICROORGANISM ONTO
COLLECTION ROD WHERE ELECTRIC FIELD IS FORMED —— S14
  ↓
SEPARATE COLLECTION ROD FROM PARTICLE
SEPARATION DEVICE —— S15
  ↓
INSERT COLLECTION ROD INTO REAGENT
CONTAINER TO ALLOW COLLECTION ROD TO REACT —— S16
WITH LYSIS REAGENT AND LUMINOUS MATERIAL
  ↓
MEASURE INTENSITY OF LIGHT/ DETECT
MICROBIAL CONCENTRATION BY USING —— S17
LUMINESCENCE MEASUREMTN DEVICE
  ↓
END
```

AIRBORNE MICROBIAL MEASUREMENT APPARATUS AND MEASUREMENT METHOD

This application is a National Stage Application of International Application No. PCT/KR2014/012421, filed on Dec. 16, 2014, which claims the benefit of Korean Patent Application No. 10-2014-0023203, filed on Feb. 27, 2014, all of which are hereby incorporated by reference in their entirety for all purposes as if fully set forth herein.

TECHNICAL FIELD

The present disclosure relates to an airborne microbial measurement apparatus and method.

BACKGROUND ART

In recent years, as avian influenza and new type influenza are issued, aerial infection problems are becoming the main issue of society. For this reason, the subject with regard to a method of measuring airborne microbial particles in air is importantly treated, and a biosensor market is sharply growing accordingly.

As the existing method of measuring airborne microbial particles in air, there are a culture method in which airborne bioparticles in a sample gas are collected onto a surface of a solid or liquid suitable for growth to culture the collected bioparticles under an appropriate temperature-humidity condition for a predetermine time, thereby calculating the number of collected microorganism from the number of colony generated on the surface and a staining method in which bioparticles are stained to measure the number of microorganism by using a fluorescence microscope.

Recently, an adenosine triphosphate (ATP) bioluminescence method using a principle in which ATP reacts with luciferin/luciferase to emit light may be developed to allow a series of processes including ATP elimination process, ATP extraction, and luminescence amount measurement to be performed within about thirty minutes, thereby implementing rapid working.

However, according to the above-described methods, the airborne microbial particles existing in the air may not be measured in real time, and a series of handworks including a separate sampling process and pretreatment process is required. Thus, there is a limitation in that a system of automatically measuring the airborne microbial particles in the air can not be developed by using these methods.

Figure 1:
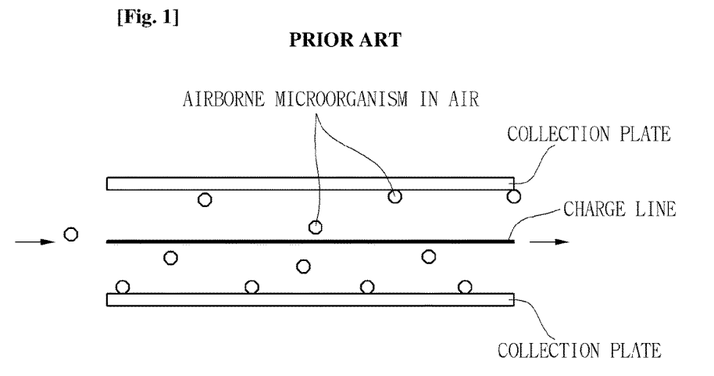
FIG. 1 is a view of an electric dust collector provided in an particle separation device according to a related art.

FIG. 1 is a view of an electric dust collector provided in an particle separation device according to a related art.

Referring to FIG. 1, an electric dust collector according to the related art includes collection plates disposed on both sides thereof and a charge line (a discharge electrode) disposed between the collection plates disposed on both sides thereof.

When a high voltage is applied to the charge line, corona discharge occurs to generate ions. Here, predetermined particles in a gas are charged by the generated ions. Also, the charged particles may move and be collected to a dust collection electrode (the collection plate) by an electric force. That is, the electric dust collector may be understood as a dust collecting device that is capable of collecting predetermined particles using an electrostatic principle. The predetermined particles may include foreign substances such as dusts or airborne microorganism.

The airborne microbial measurement apparatus according to the related art includes the electric dust collector and a collection rod for collecting the microorganism collected onto the collection plate. In the airborne microbial measurement apparatus according to the related art, when the airborne microorganism is collected onto the collection plate by driving of the electric dust collector, a user manually put the collection rod into contact with the collection plate to collect or sample the airborne microorganism. Also, the collected airborne microorganism reacts with a lysis reagent to emit light. Here, the measurement apparatus detects the emitted light to measure a concentration of the microorganism.

Like this, in the case of the airborne microbial measurement apparatus according to the related art, since the collection rod has to be separately provided, and also the user has to collect the airborne microorganism collected onto the collection plate by using the collection rod, it takes a lot of time and also comes expensive.

DISCLOSURE OF INVENTION

Technical Problem

Embodiments provide an airborne microbial measurement apparatus that is capable of rapidly measuring airborne microbial particles existing in air and an airborne microbial measurement method.

Solution to Problem

In one embodiment, an airborne microbial measurement apparatus includes: a particle separation device including a main body having a flow space in which airborne microorganism flows and a collection unit separably coupled to one side of the main body to collect the airborne microorganism; a reagent container in which a lysis reagent reacting with the airborne microorganism collected in the collection unit and a luminous material are stored; and a luminescence measurement device for measuring intensity of light emitted after the airborne microorganism reacts with the lysis reagent and the luminous material.

Also, the collection unit may include: a collection body having an inflow hole into which air containing the airborne microorganism is introduced; and a collection rod disposed on the collection body and in the flow space.

Also, the particle separation device may include an electric charge part disposed on one side of the inflow hole to electrically charge the airborne microorganism.

Also, the electric part may include: a ground electrode; and a discharge wire disposed to be spaced apart from the ground electrode.

Also, each of the ground electrode and the discharge wire may be provided in plurality, and the plurality of ground electrodes and discharge wires may be alternately disposed.

Also, the collection unit may further include a support member coupled to the collection body to support the collection rod, and the collection rod may extend from the support member toward the flow space.

The main body of the particle separation device may have an insertion hole communicating with the inflow hole is defined, and the flow space may define an inner space of the inflow hole.

Also, the collection rod may extend along a central portion of the flow space.

Also, the particle separation device may include a flow generation unit disposed at one side of the flow space to generate a flow of the air.

Also, the flow generation unit may include a fan.

Also, the airborne microbial measurement apparatus may further include: at least one guide member coupled to the collection body to guide coupling of the collection rod and the main body; and a guide member insertion part defined in the main body to allow the guide member to be inserted thereto.

Also, the collection unit may include an inertial impactor or a cyclone, and the inertial impactor may include an acceleration nozzle and an impaction plate disposed under the acceleration nozzle.

In another embodiment, a method of measuring airborne microorganism includes: collecting the airborne microorganism onto a collection rod while air containing the airborne microorganism flows; separating the collection rod from a main body of a particle separation device; coupling the collection rod to a reagent container to allow the airborne microorganism of the collection rod to react with a lysis reagent and a luminous material; and measuring intensity of light emitted after the reaction by using a luminescence measurement device.

Also, the collecting of the airborne microorganism may include applying a voltage into an electric charge part including a ground electrode and a discharge wire.

Also, the collecting of the airborne microorganism may further include operating a flow generation unit to allow the air containing the airborne microorganism to pass through the electric charge part so that the air is electrically charged and to flow into a flow space in which the collection rod is disposed.

In further another embodiment, an airborne microbial measurement apparatus includes: a particle separation device separating airborne microorganism from air; a reagent container in which a lysis reagent reacting with the airborne microorganism separated from the particle separation device and a luminous material are stored; and a luminescence measurement device for measuring intensity of light emitted by the reaction between the airborne microorganism and the lysis reagent and luminous material, wherein the particle separation device may include: an inflow hole into which the airborne microorganism is introduced; a flow generation unit for generating a flow of the air so as to introduce the airborne microorganism through the inflow hole; an electric charge part disposed at one side of the inflow hole to electrically charge the airborne microorganism; and a collection rod disposed between the electric charge part and the flow generation unit to collect the airborne microorganism electrically charged by the electric charge part.

Also, a voltage having polarity opposite to that of a voltage applied into the electric charge may be applied to the collection rod.

Also, the particle separation device may further include a main body having a flow space in which the airborne microorganism that is electrically charged by the electric charge part flows, and the collection rod may be disposed in the flow space.

Also, the airborne microbial measurement device may further include at least one guide member disposed to be spaced from the collection rod.

Also, the main body may include: an insertion hole into which the collection rod is inserted; and a guide member insertion part into which the guide member is inserted.

Advantageous Effects of Invention

According to the airborne microbial measurement apparatus and method, the user may separate the collection rod itself from the main body of the particle separation device to put the separated the collection rod into the lysis container without manually sampling the airborne microorganism collected onto the collection plate. Thus, the time taken for measuring may be reduced, and also the airborne microbial measurement process may be simply performed.

Also, since the reagent container for storing the reagent for lysing the airborne microorganism to extract the ATP and the luminous material emitting the light by reacting with the ATP is provided, and the collection rod is put into the reagent container to perform the ATP extraction and the luminescence operation at once, the process for measuring may be simplified.

Also, since the unit for generating the flow of the air is disposed in the particle separation device, and the collection rod is disposed between the electric charge part and the air flow generation unit, a series of processes in which when the air flow generation unit is driven the airborne microorganism is electrically charged in the electric charge part and is collected onto the collection rod may be performed in a short time.

Also, the air flow generation unit may be provided as the fan to realize the miniaturized and lightweight air flow generation unit when compared to a case of using the air pump.

MODE FOR THE INVENTION

Hereinafter, reference will now be made in detail to the embodiments of the present invention, examples of which are illustrated in the accompanying drawings. The invention may, however, be embodied in many different forms and should not be construed as being limited to the embodiments set forth herein; rather, that alternate embodiments included in other retrogressive inventions or falling within the spirit and scope of the inventive concept will fully convey the concept of the invention to those skilled in the art.

Figure 2:
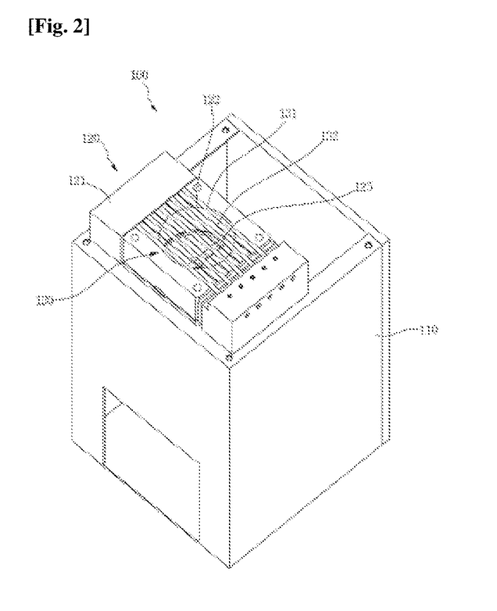
FIG. 2 is a perspective view of the particle separation device according to an embodiment.
Figure 3:
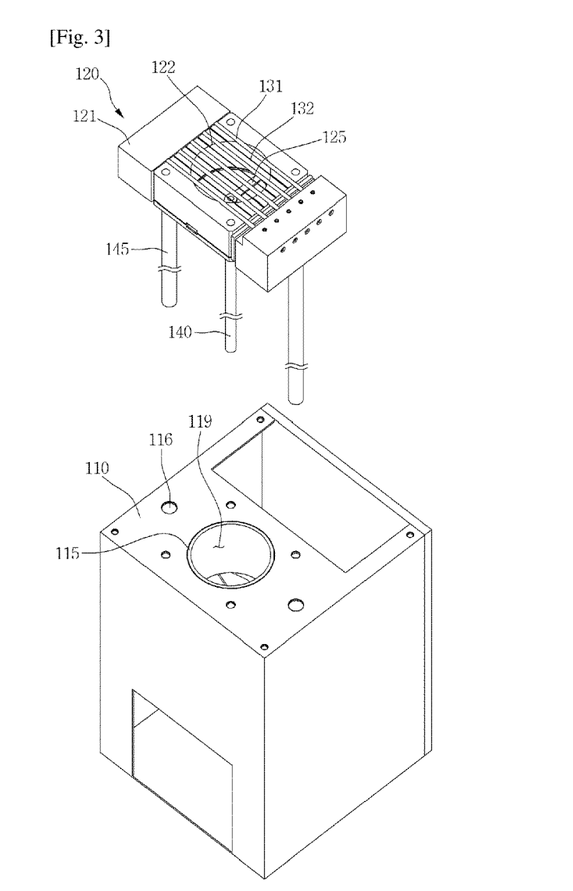
FIG. 3 is an exploded perspective view illustrating the particle separation device according to an embodiment.
Figure 4:
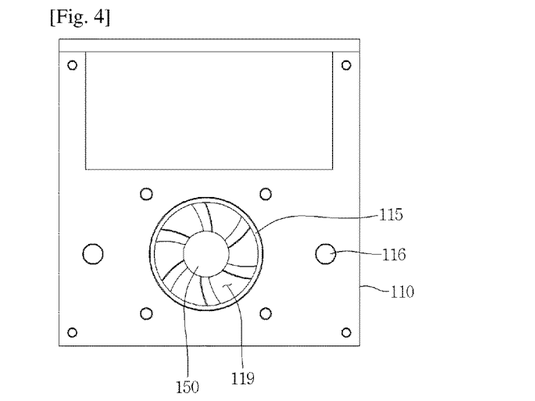
FIG. 4 is a plan view of a fan of the particle separation device according to an embodiment.

FIG. 2 is a perspective view of the particle separation device according to an embodiment, FIG. 3 is an exploded perspective view illustrating the particle separation device according to an embodiment, and FIG. 4 is a plan view of a fan of the particle separation device according to an embodiment.

Referring to FIGS. 2 to 4, a particle separation device 100 according to an embodiment includes a main body 110 in which a power source supply part (not shown) is disposed and a collection unit 120 separably coupled to the main body 110. The collection unit 120 includes a collection body 121 disposed on an upper portion of the main body 110 and an electric charge part 130 coupled to the collection body 121.

In detail, an inflow hole 122 into which air containing an airborne microorganism is defined in the collection body 121. Also, a flow generation unit 150 for generating a flow of air is disposed on a lower portion of the main body 110. When the flow generation unit 150 operates, the air outside the particle separation device 100 may be introduced into the main body 110 through the inflow hole 122.

The electric charge part 130 includes a ground electrode 131 and a discharge wire 132 which is a discharge electrode that is disposed to be spaced apart from the ground electrode 131. The ground electrode 131 and the discharge wire 132 may be provided in plurality. Also, the plurality of ground electrodes 131 and the plurality of discharge wires 132 may be alternately disposed.

Also, the plurality of ground electrodes 131 and the plurality of discharge wires 132 may be disposed above the inflow hole 122. When the electric charge part 130 is driven while the air containing the airborne microorganism is introduced into the inflow hole 122, the airborne microorganism is electrically charged to move into the main body 110.

In detail, when the electric charge part 130 is driven, a high voltage is applied from the power source supply part to the discharge wire 132 to cause corona discharge due to a voltage difference between the ground electrode 131 and the discharge wire 132. Also, negative (−) or positive (+) ions generated when the corona discharge occurs may be charged with airborne microorganism, and thus the airborne microorganism may be electrically charged. The electrically charged airborne microorganism may flow into the main body 110 through the inflow hole 122 and be collected onto a collection rod 140.

The collection unit 120 includes the collection rod 140 on which the electrically charged airborne microorganism is collected and a support member 125 for supporting the collection rod 140 on the collection body 121. The support member 125 is coupled to the collection body 121 at a lower side of the inflow hole 122. Also, the collection rod 140 is coupled to the support member 125 to extend downward. That is, the collection rod 140 has one end that is coupled to the support member 125 and the other end that is disposed in the main body 110.

Also, the collection rod 140 may be disposed between the electric charge part 130 disposed on the upper portion of the collection unit 120 and the flow generation unit 150 disposed on the lower portion of the main body 110, with respect to a moving path of the airborne microorganism. According to the above-described arrangement, when the flow generation unit 150 is driven, the airborne microorganism in the air may be electrically charged by the electric charge part 130 and then be collected onto the collection rod 140. Also, the air may pass through the flow generation unit 150 and be discharged to the outside.

Also, the collection rod 140 may extend downward from an approximately central portion of the inflow hole 122. Thus, the airborne microorganism electrically charged while passing through the inflow hole 122 may be easily collected onto the collection rod 140.

A voltage having polarity opposite to that of the voltage applied to the discharge wire 132 may be applied to the collection rod 140. For example, when the voltage applied to the discharge wire 132 corresponds to a positive (+) voltage, and the airborne microorganism is electrically charged with positive (+) ions, a negative (−) voltage may be applied to the collection rod 140. On the other hand, when the voltage applied to the discharge wire 132 corresponds to a negative (−) voltage, and the airborne microorganism is electrically charged with negative (−) ions, a positive (+) voltage may be applied to the collection rod 140. According to the structure, the electrically charged airborne microorganism may be easily collected onto the collection rod 140 having an electric field having polarity opposite thereto.

The collection unit 120 may further include a guide member 145 for guiding a coupling position at the main body 110. For example, the guide member 145 may be provided in plurality, and the plurality of guide members 145 may be spaced apart from each other at both sides of the collection rod 140 and coupled to a bottom surface of the collection body 121 to extend downward.

The main body 110 includes a guide member insertion part 116 into which the guide member 145 is inserted. The guide member insertion part 116 may be recessed downward from both sides of a top surface of the main body 110 and may have a size slightly greater than a diameter of the guide member 145 so that the guide member 145 is easily inserted thereto.

The main body 110 includes an insertion hole 115 into which the collection rod 140 is inserted and a flow space 119 recessed downward from the insertion hole 115. The insertion hole 115 communicates with the inflow hole 122 and defines an inlet of the flow space 119. Also, the insertion hole 115 may have a size approximately similar to that of the inflow hole 122. Also, the flow space 119 may have an approximately cylindrical shape.

Each of the insertion hole 115 and the flow space 119 may have a diameter or size that is sufficiently greater than the diameter of the collection rod 140. Also, the flow space 119 may define a space through which the air introduced through the inflow hole 122 flows and may define space in which electrostatic gravity is applied so as to allow the electrically charged airborne microorganism is collected onto the collection rod 140.

Hereinafter, a process in which the collection unit 120 is coupled to and separated from the main body 110 will be simply described.

Since the guide member 145 is fitted into the guide member insertion part 116 by a user in a state where the collection unit 120 is separated from the main body 110, the user may easily confirm the coupling position of the collection unit 120.

When the guide member 145 is inserted into the guide member insertion part 116, the collection rod 140 may be accommodated into the flow space 119 through the insertion hole 115. Here, the collection rod 140 may be disposed to extend downward along a central portion of the flow space 119. Since the collection rod 140 is disposed along the central portion of the flow space 119, that is, since the collection rod 140 and the flow space 119 are coaxially disposed, the electrically airborne microorganism that is introduced through the insertion hole 115 may be easily collected onto the collection rod 140.

If the collection rod 140 is eccentrically disposed from the center of the flow space 119, the airborne microorganism flowing out of a range of the electric field formed around the collection rod 140 may be difficult to be collected onto the collection rod 140. The current embodiment may solve the above-described limitation.

When the collection unit 120 is coupled to the main body 110, the collection body 121 may be supported by the upper portion of the main body 110, and also the inflow hole 122 may communicate with the insertion hole 115. When it is intended to separate the collection unit 120 from the main body 110, the user may grasp the collection body 121 to pick the collection body 121 upward, thereby easily separating the collection unit 120 from the main body 110.

The flow generation unit 150 for generating the flow of air is disposed on the lower portion of the main body 110. The flow generation unit 150 may be disposed on a lower end of the flow space 119. For example, the flow generation unit 150 includes a fan. The fan may be understood as a lightweight and small scale structure when compared to the air pump.

The flow generation unit 150 provides a driving force for allowing outdoor air to flow into the flow space 119 through the inflow hole 122 and the insertion hole 115. The air passing through the flow space 119 may be discharged from the main body 110 through the flow generation unit 150.

Figure 5:
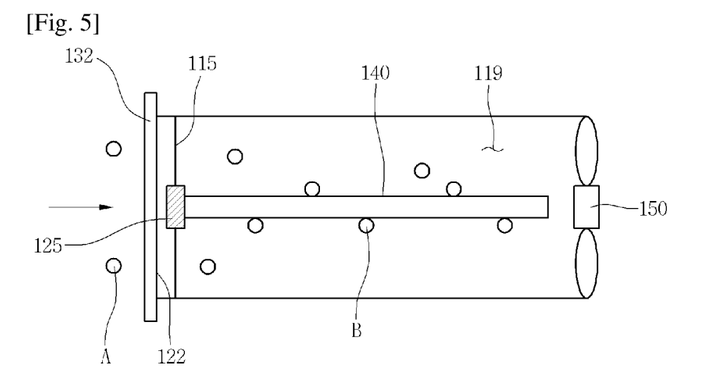
FIG. 5 is a schematic view illustrating an operation of the particle separation device according to an embodiment.
Figure 6:
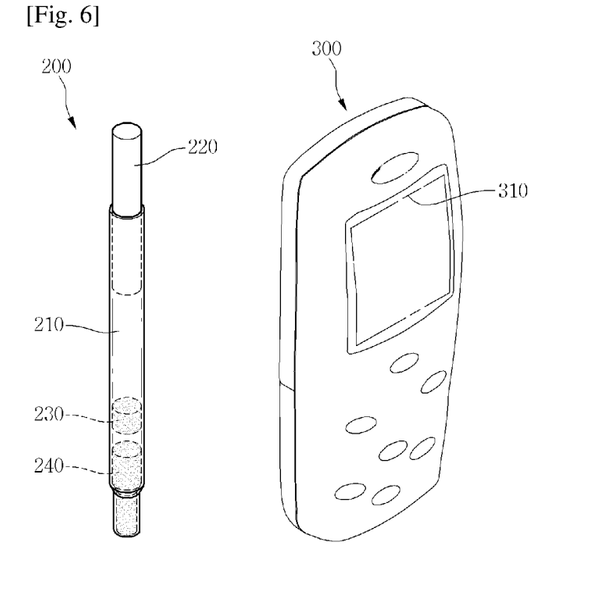
FIG. 6 is a view of a reagent container and a luminescence measurement device according to an embodiment.

FIG. 5 is a schematic view illustrating an operation of the particle separation device according to an embodiment, and FIG. 6 is a view of a reagent container and a luminescence measurement device according to an embodiment.

Referring to FIG. 5, a process for collecting the airborne microorganism in the air will be simply described. When the voltage is applied to the discharge wire 132 to operate the electric charge part 130, thereby driving the flow generation unit 150, the airborne microorganism A in the air may be electrically charged while passing through the electric charge part 130. Also, the electrically charged airborne microorganism B may flow toward the collection rod 140 due to the electric field formed around the collection rod 140 and then be attached to a surface of the collection rod 140.

The above-described collection process may be performed during a preset time. After the collection process is completed, the electric charge part 130 and the flow generation unit 150 may be turned off.

Also, the user may grasp the collection body 121 to separate the collection unit 120 from the main body 110. The collection rod 140 of the separated collection unit 120 may be put into a reagent container 200.

In detail, the airborne microbial measurement apparatus according to an embodiment includes the reagent container 200 in which a plurality of reagents are disposed and a luminescence measurement device 300 that is put into the reagent container 200 to measure intensity of the emitted light.

The reagent container 200 includes a container body 210 in which the plurality of reagents are stored and a stopper 220 for blocking an opened upper portion of the container body 210. The plurality of reagents includes a lysis reagent 230 for lysing cells (or cell walls) of the airborne microorganism and a luminous material 240 for emitting light by reacting with adenosine triphosphate (ATP) that is extracted from the lysed cells.

The luminous material includes luciferin and luciferase. The luciferin is activated by the ATP existing in the lysed cells to change into active luciferin. The active luciferin is oxidized by the effect of the luciferase that is a luminous enzyme to become oxide luciferin. Here, chemical energy is converted into light energy to emit the light.

The luminous material 240 may be disposed in a lower portion of the container body 210. The lysis reagent 230 may be disposed at an upper side of the luminous material 240. The luminous material 240 and the lysis reagent 230 may form a boundary surface therebetween. Alternatively, the luminous material 240 and the lysis reagent 230 may be disposed to be spaced apart from each other with a predetermined separator (or a separation material) therebetween.

The collection rod 140 may be put into the container body 210 through the opened upper portion of the container body 210. When the collection rod 140 is put, the airborne microorganism of the collection rod 140 may firstly react with the lysis reagent 230 to lyse the cells, and thus the ATP is exposed or extracted. Also, the extracted ATP reacts with the luminous material to emit the light.

Intensity of the emitted light may be measured by the luminescence measurement device 300. Here, concentration or a degree of contamination of the microorganism may be calculated through the measured intensity of the light. The luminescence measurement device 300 includes a photo diode (PD) or a light receiving device such as an avalanche photo diode (APD) which convert light into electricity.

Also, the luminescence measurement device 300 may further include a display part 310 displaying the measured intensity of light, the concentration or degree of contamination of the microorganism.

Figure 7:
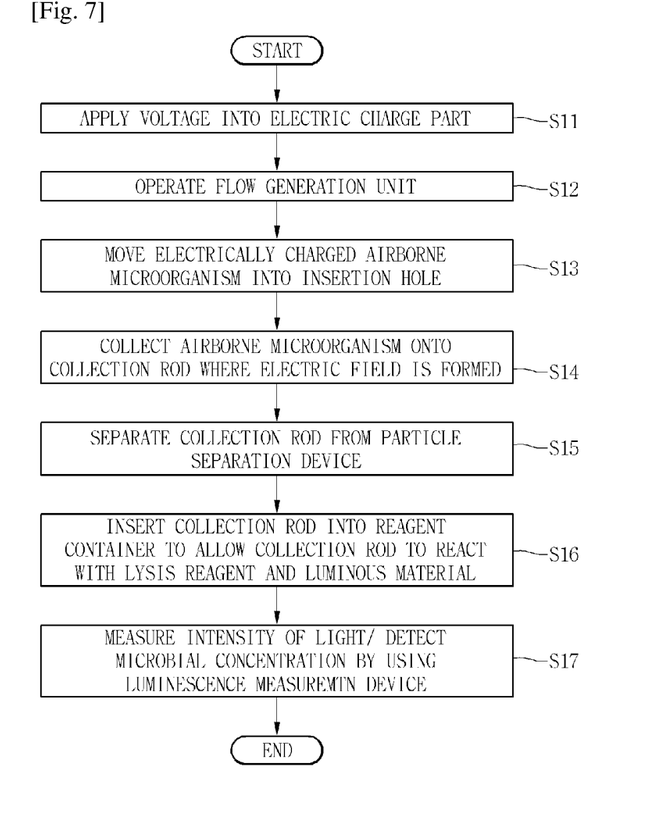
FIG. 7 is a flowchart illustrating a method of measuring airborne microorganism according to an embodiment.

FIG. 7 is a flowchart illustrating a method of measuring the airborne microorganism by using the airborne microbial measurement apparatus according to an embodiment. The method of measuring the airborne microorganism according to the current embodiment will be described with reference to FIG. 7.

First, a high voltage is applied to the electric charge part 130 according to an embodiment, i.e., the discharge wire 132 to operate the flow generation unit 150. Then, the air existing outside the particle separation device 100 may flow toward the inflow hole 122 by the driving force of the flow generation unit 150.

The air introduced into the inflow hole 122 includes the airborne microorganism. In operations S11 and S12, the airborne microorganism in the air flowing into the inflow hole 122 may be electrically charged into the positive (+) or negative (−) ions while the air passes through the electric charge part 130 disposed at an upper side of the inflow hole 122.

The electrically charged airborne microorganism is introduced into the insertion hole 115, i.e., the flow space 119. In operations S13 and S14, the collection rod 140 extends in an approximately central portion of the flow space 119, and the electrically charged airborne microorganism may be collected onto an outer surface of the collection rod 140 having the electric field having polarity opposite thereto.

When the airborne microorganism is completely collected onto the outer surface of the collection rod 140, the user may separate the collection rod 140 from the particle separation device 100. Here, whether the collection of the airborne microorganism is completed may be determined according to whether the preset time elapses.

The separated collection rod 140 may be inserted into the reagent container 200. Also, the airborne microorganism collected onto the collection rod 140 may react with the lysis reagent 230 and the luminous material 240 stored in the reagent container 200. During the reaction process, the cells (or cell walls) of the airborne microorganism may be lysed by the lysis reagent 230. As a result, the ATP of the airborne microorganism may be exposed. In operation S16, the exposed ATP may react with the luminous material 240 to emit a predetermined light.

The intensity of the light emitted form the reagent container 200 may be measured by using the luminescence measurement device 300. For example, the reagent container 200 may be coupled to the luminescence measurement device 300 or be disposed adjacent to the luminescence measurement device 300, and thus the light receiving element of the luminescence measurement device 300 may measure the intensity of the light. Also, in operation S17, the measured intensity of the light may be converted into a concentration value of the airborne microorganism and be displayed on the display part 310 of the luminescence measurement device 300.

According to the measurement apparatus and method, the user may separate the collection rod itself from the main body of the particle separation device to put the separated collection rod into the lysis container without manually sampling the airborne microorganism collected onto the collection plate. Thus, the time taken for measuring may be reduced, and also the measurement process may be simply performed.

Also, since the air flow generation unit is disposed in the particle separation device, and the collection is disposed between the electric charge part and the air flow generation unit, a series of processes in which when the air flow generation unit is driven, the airborne microorganism is electrically charged in the electric charge part and is collected onto the collection rod may be performed in a short time.

Another embodiment will be proposed.

Although the method of collecting the airborne microorganism into the collection rod in the electrical dust collecting manner is adopted in the above-described embodiment, different methods of collecting the airborne microorganism onto the collection rod may be adopted.

For example, the collection unit may include an inertial impactor to adopt a method of collecting the airborne microorganism by using an inertial force. In detail, the inertial impactor has a structure in which an impaction plate or a receiving tube (a collection rode) is disposed under an acceleration nozzle (an impaction nozzle).

A flow direction of the air passing through the acceleration nozzle or a jet may be switched at an angle of 90° by the receiving tube. Here, particles each of which has a predetermined weight of the particles contained in the air may collide with and collected into the receiving tube without being fully switched in flow direction due to the inertia thereof.

As another example, a method of collecting the microorganism by using a cyclone device may be adopted. The cyclone device may be understood as one of separation devices using a centrifugal force that is widely used to separate solid particles from a fluid or separate a gas from a liquid droplet.

In detail, the air containing the particles may be introduced into a circular cyclone in a tangential direction to flow along a cylindrical inner wall of the cyclone, thereby forming a swirl flow. The swirl flow may be maintained to a cone area in a lower portion of the cyclone to push the particles toward the inner wall by the centrifugal force, thereby separating the particles from the swirl flow. The air from which the particles are removed may ascend from a lower end of the cone toward an upper side and be discharged through an outlet. Here, the separated particles may descend along an inner wall of the cone and be collected onto a dust hopper (the collection rod).

As another example, a method of collecting the microorganism by using a centrifugal separator may be adopted. The centrifugal separator may be a device that uses a continuous centrifugal force generated while an object continuously rotates at a rapid rate. The cyclone may also be a separator using the centrifugal force. However the centrifugal separator may separate the particles contained in the air toward an outer wall of a rotation container by using the rotation container that rotates at a relatively high rate when compared to the cyclone.

INDUSTRIAL APPLICABILITY

According to the airborne microbial measurement apparatus and method, the user may separate the collection rod itself from the main body of the particle separation device to put the separated the collection rod into the lysis container without manually sampling the airborne microorganism collected onto the collection plate. Thus, the time taken for measuring may be reduced, and also the airborne microbial measurement process may be simply performed. Therefore, industrial applicability is significantly high.

The invention claimed is:

1. An airborne microbial measurement apparatus comprising:
   a particle separation device comprising a main body having a flow space in which airborne microorganism flows and a collection unit separably coupled to the main body to collect the airborne microorganism;
   a reagent container including a container body having an opened upper portion, the container body being configured to store a lysis reagent reacting with the airborne microorganism collected in the collection unit and a luminous material are stored; and
   a luminescence measurement device for measuring intensity of light emitted after the airborne microorganism reacts with the lysis reagent and the luminous material, wherein:
   the collection unit includes a collection body having an inflow hole into which air containing the airborne microorganism is introduced, an electric charge part disposed at a side of the inflow hole to electrically charge the airborne microorganism and a collection rod disposed in the flow space and extended longitudinally to collect the charged airborne microorganism by the electric charge part, and
   the lysis reagent is disposed at an upper side of the luminous material in the container body, and
   when the collection rod is disposed inside the container body through the opened upper portion, the airborne microorganism of the collection rod first reacts with the lysis reagent to lyse the cells and to allow ATP to be extracted, and then the extracted ATP reacts with the luminous material to emit the light.

2. The airborne microbial measurement apparatus according to claim 1, wherein the electric part comprises:
   a ground electrode; and
   a discharge wire disposed to be spaced apart from the ground electrode.

3. The airborne microbial measurement apparatus according to claim 2, wherein each of the ground electrode and the discharge wire is provided in plurality, and the plurality of ground electrodes and discharge wires are alternately disposed.

4. The airborne microbial measurement apparatus according to claim 1, wherein the collection unit further comprises a support member coupled to the collection body to support the collection rod, and
   the collection rod extends from the support member toward the flow space.

5. The airborne microbial measurement apparatus according to claim 1, wherein the main body of the particle separation device has an insertion hole communicating with the inflow hole, and the flow space defines an inner space of the inflow hole.

6. The airborne microbial measurement apparatus according to claim 5, wherein the collection rod extends along a central portion of the flow space.

7. The airborne microbial measurement apparatus according to claim 1, wherein the particle separation device comprises a flow generation unit disposed at one side of the flow space to generate a flow of the air.

8. The airborne microbial measurement apparatus according to claim 1, wherein the flow generation unit comprises a fan.

9. The airborne microbial measurement apparatus according to claim 1, further comprising:
- at least one guide member coupled to the collection body to guide coupling of the collection rod and the main body; and
- a guide member insertion part defined in the main body to allow the guide member to be inserted thereto.

10. The airborne microbial measurement apparatus according to claim 1, wherein the collection unit comprises an inertial impactor or a cyclone, and
- the inertial impactor comprises an acceleration nozzle and an impaction plate disposed under the acceleration nozzle.

* * * * *